US012781257B2

(12) United States Patent
Kusakabe et al.

(10) Patent No.: US 12,781,257 B2
(45) Date of Patent: Nov. 3, 2026

(54) METHOD FOR MEASURING L-ASPARAGINE AND KIT FOR THE SAME

(71) Applicant: ENZYME-SENSOR CO., LTD., Tsukuba (JP)

(72) Inventors: Hitoshi Kusakabe, Tsukuba (JP); Keiko Shintate, Tsukuba (JP); Woro Triarsi Sulistyaningdyah, Tsukuba (JP); Tatsuya Nishiyama, Kawasaki (JP); Kenji Ueda, Machida (JP)

(73) Assignee: ENZYME-SENSOR CO., LTD., Tsukuba (JP)

( * ) Notice: Subject to any disclaimer, the term of this patent is extended or adjusted under 35 U.S.C. 154(b) by 295 days.

(21) Appl. No.: 18/730,163

(22) PCT Filed: Jan. 19, 2023

(86) PCT No.: PCT/JP2023/001420
§ 371 (c)(1),
(2) Date: Jul. 18, 2024

(87) PCT Pub. No.: WO2023/140305
PCT Pub. Date: Jul. 27, 2023

(65) Prior Publication Data

US 2025/0115944 A1 Apr. 10, 2025

(30) Foreign Application Priority Data

Jan. 20, 2022 (JP) ................................ 2022-007121

(51) Int. Cl.
*C12Q 1/28* (2006.01)
*C12Q 1/34* (2006.01)

(52) U.S. Cl.
CPC ................ *C12Q 1/28* (2013.01); *C12Q 1/34* (2013.01)

(58) Field of Classification Search
None
See application file for complete search history.

(56) References Cited

FOREIGN PATENT DOCUMENTS

JP 2010-207168 A 9/2010
JP 6585244 B1 10/2019
(Continued)

OTHER PUBLICATIONS

Bergmeyer ("L-Aspartate and L-Asparagine", Methods of Enzymatic Analysis (Second English Edition), vol. 4, 1974, Academic Press, New York, New York, 1696-1700). (Year: 1974).*
(Continued)

*Primary Examiner* — Robert J Yamasaki
*Assistant Examiner* — Charles Zotlan Constantine
(74) *Attorney, Agent, or Firm* — WHDA, LLP

(57) ABSTRACT

There is provided a method for measuring L-asparagine contained in a sample such as foods by using enzymes. There is provided a method with which L-glutamine, L-glutamic acid and L-aspartic acid can be distinguished from L-asparagine and removed, so that L-asparagine alone can be measured. There is provided a kit for measuring L-asparagine contained in a sample, which comprises the following solution A and solution B: (Solution A) a solution containing aspartate transaminase (GOT), glutaminase, L-glutamate oxidase, catalase, ascorbate oxidase, and α-ketoglutaric acid; and (Solution B) a solution containing asparaginase, peroxidase, and a catalase inactivator; provided that one of the solution A and solution B contains a coupler compound, and the other contains a new Trinder's reagent. The method of the present invention is also suitable for quantification of asparagine contained in raw materials for processed foods such as agricultural products.

10 Claims, 6 Drawing Sheets

Specification includes a Sequence Listing.

(56) References Cited

FOREIGN PATENT DOCUMENTS

| | | | |
|---|---|---|---|
| JP | 6703721 | B1 | 6/2020 |
| JP | 6703722 | B1 | 6/2020 |
| JP | 2020-129969 | A | 8/2020 |
| JP | 2020-202825 | A | 12/2020 |

OTHER PUBLICATIONS

Codex Committee on Food Additives and Contaminants, The 38th Session of the Codex Alimentarius Commission, Discussion Document CX/FAC 06/38/35, 2006, Cited in the specification. (25 pages).

Bio Vision, Asparagine Assay Kit (Fluorometric), Catalog #K736-100, 2019, Cited in the specification. (2 pages).

Megazyme, L-Asparagine, L-Glutamine, Ammonia Assay Kit Rapid, 2024, Cited in the specification. (5 pages).

Kojima Y, et al., The Journal of Laboratory and Clinical Medicine, 1969, vol. 74, No. 3, pp. 521-526, Cited in ISR. (7 pages).

Nishiyama, the Annual Meeting of Japan Society for Bioscience, Biotechnology, and Agrochemistry, 2021, vol. 2021, 3E06-10, Cited in ISR. (1 pages).

International Search Report dated Apr. 4, 2023, issued in counterpart Application No. PCT/JP2023/001420. (17 pages).

International Preliminary Report on Patentability (Form PCT/IB/373) issued in counterpart International Application No. PCT/JP2023/001420 dated Jul. 23, 2024, with Form PCT/ISA/237. (10 pages).

* cited by examiner

[Fig. 1]
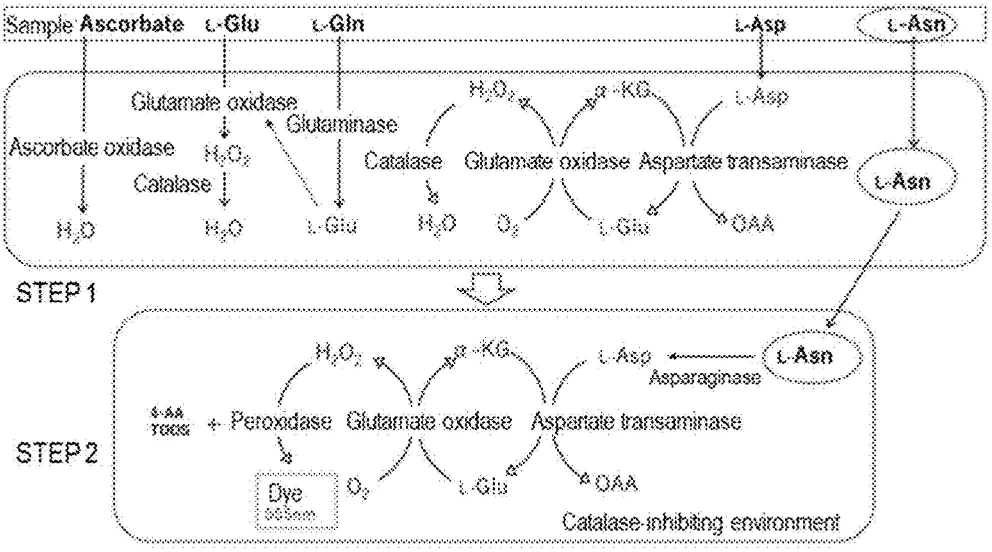
[Fig. 2]
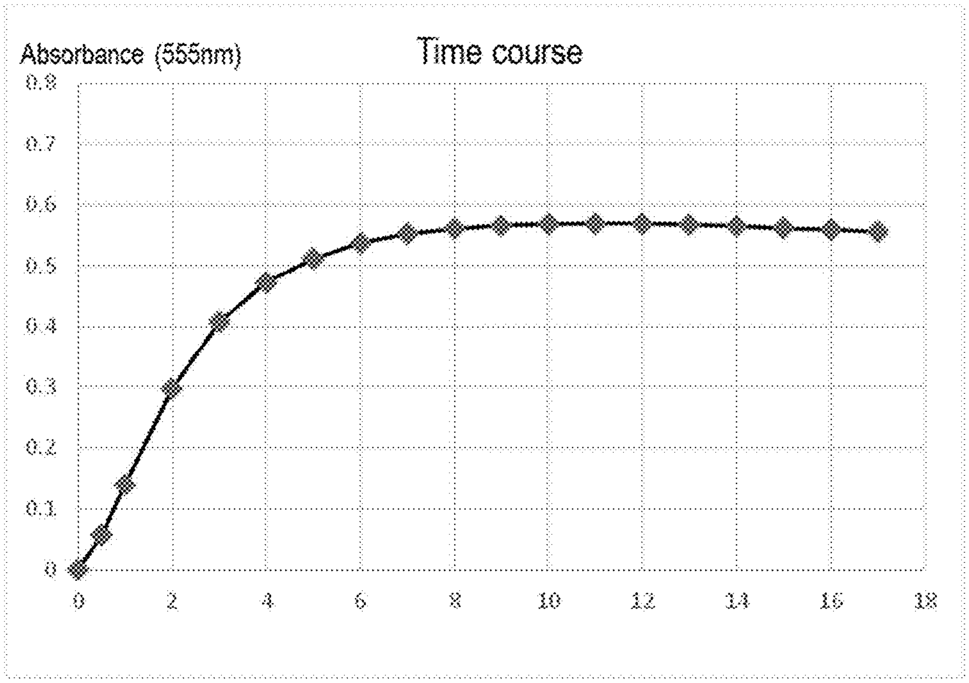

[Fig. 3]
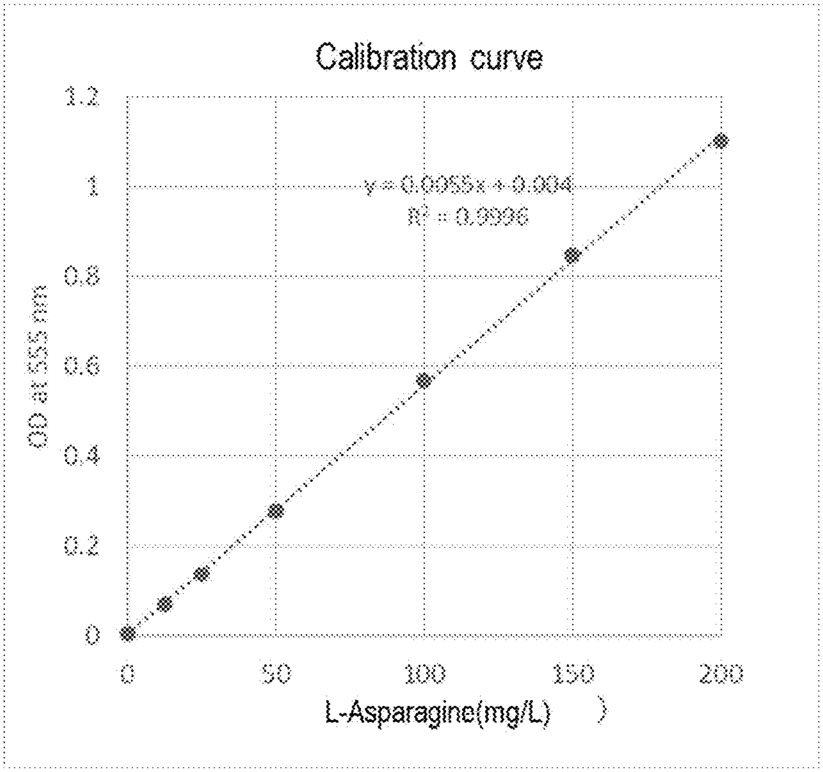
[Fig. 4]
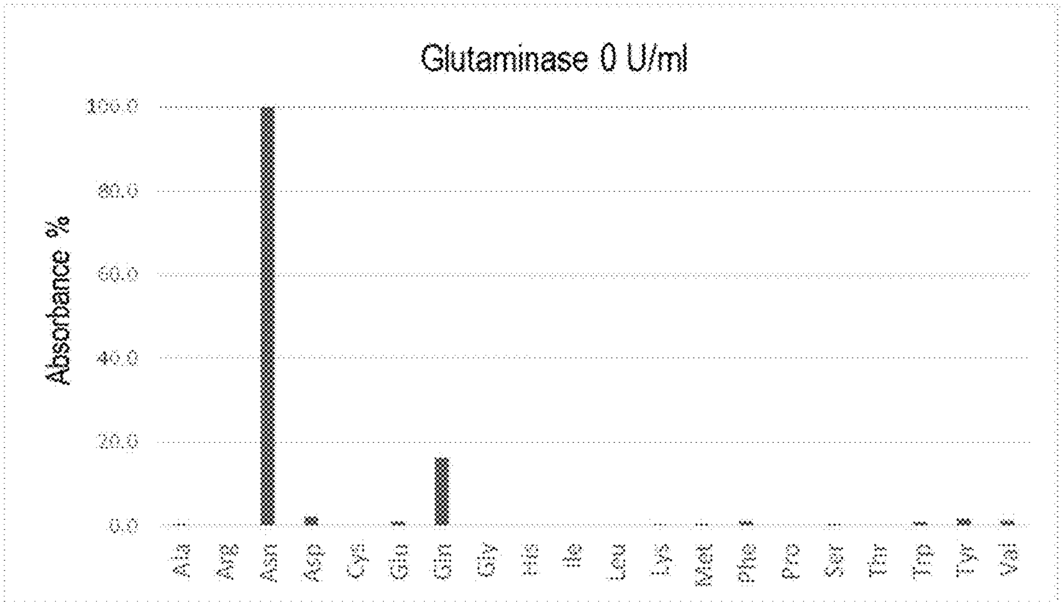

[Fig. 5]
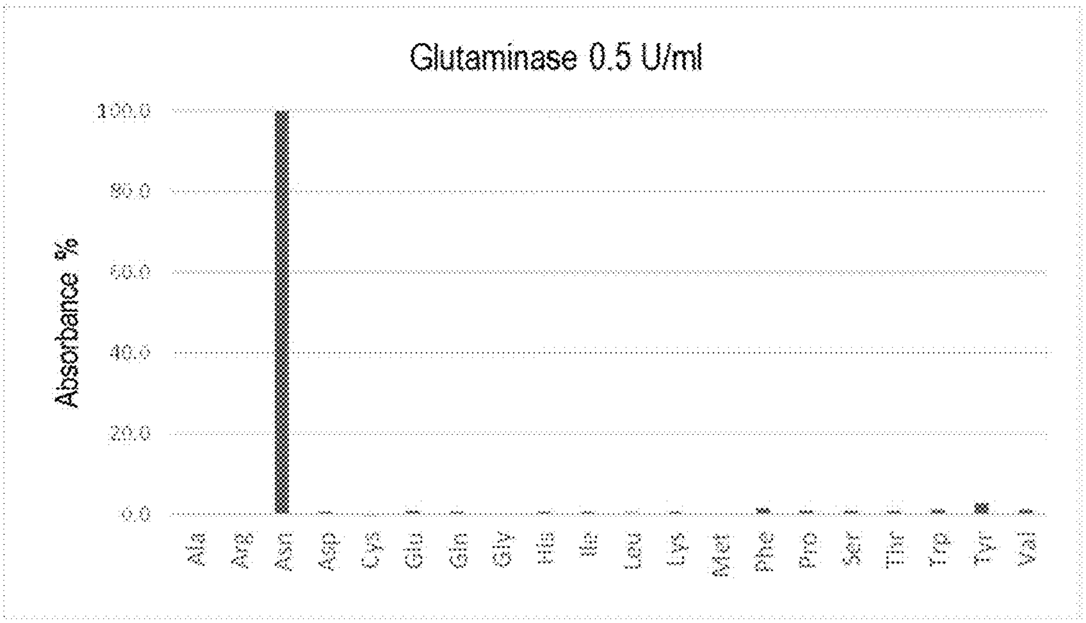
[Fig. 6]
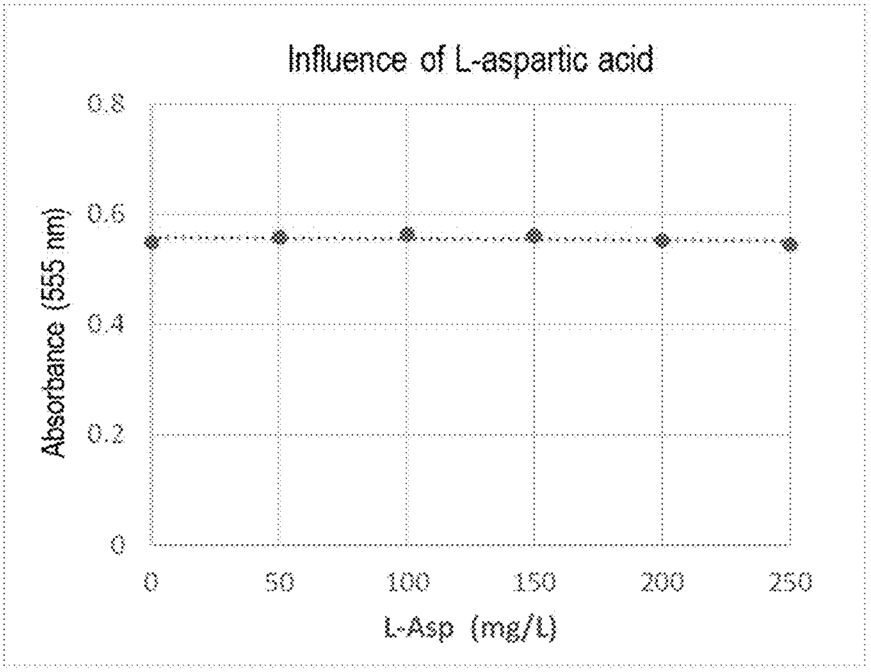

[Fig. 7]
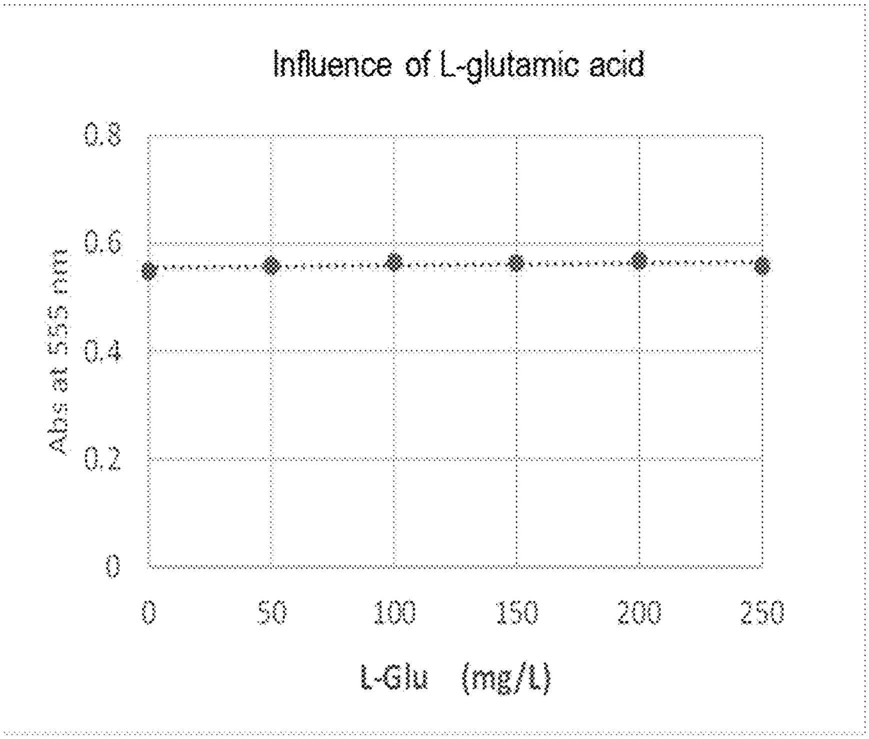
[Fig. 8]
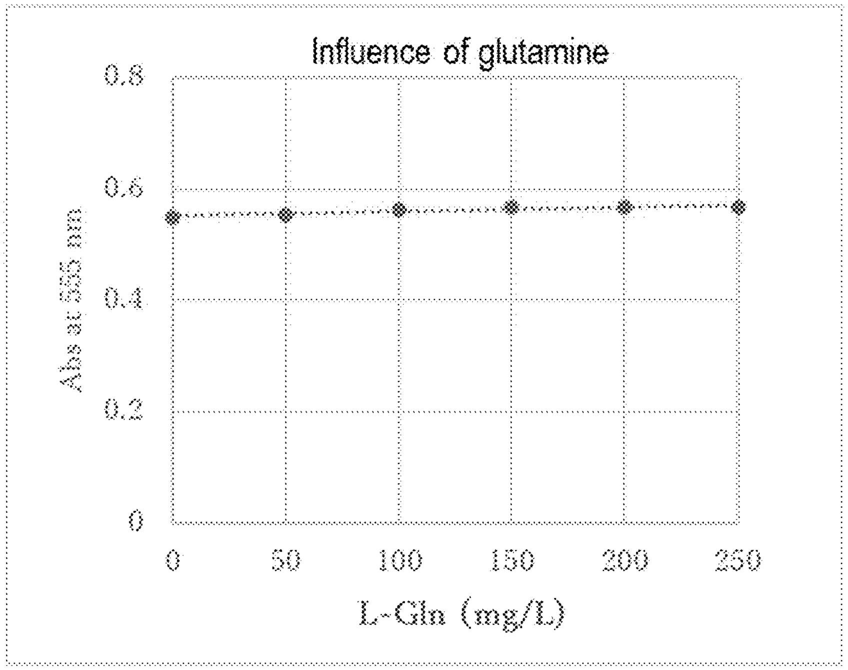

[Fig. 9]
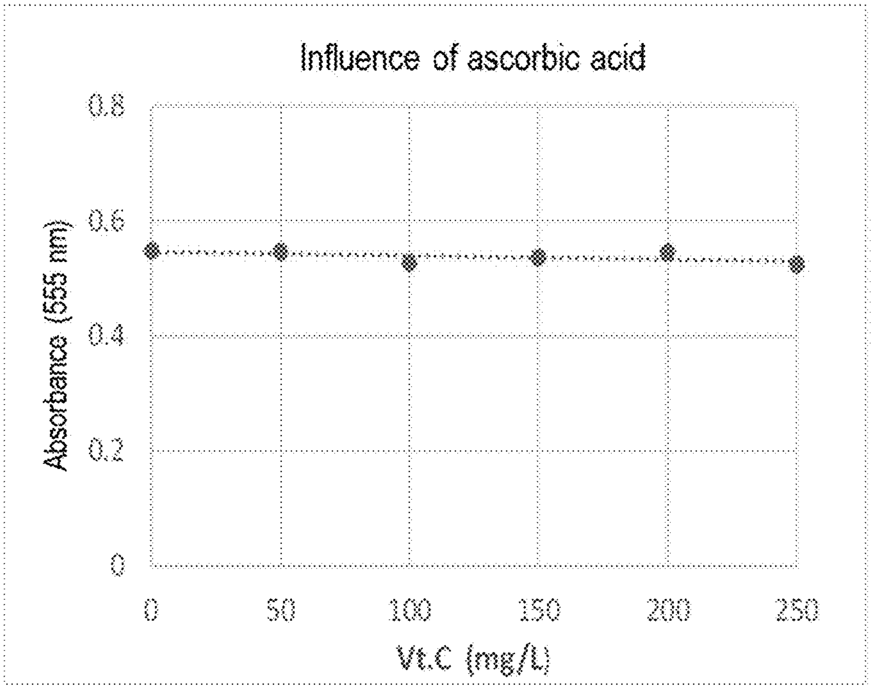
[Fig. 10]
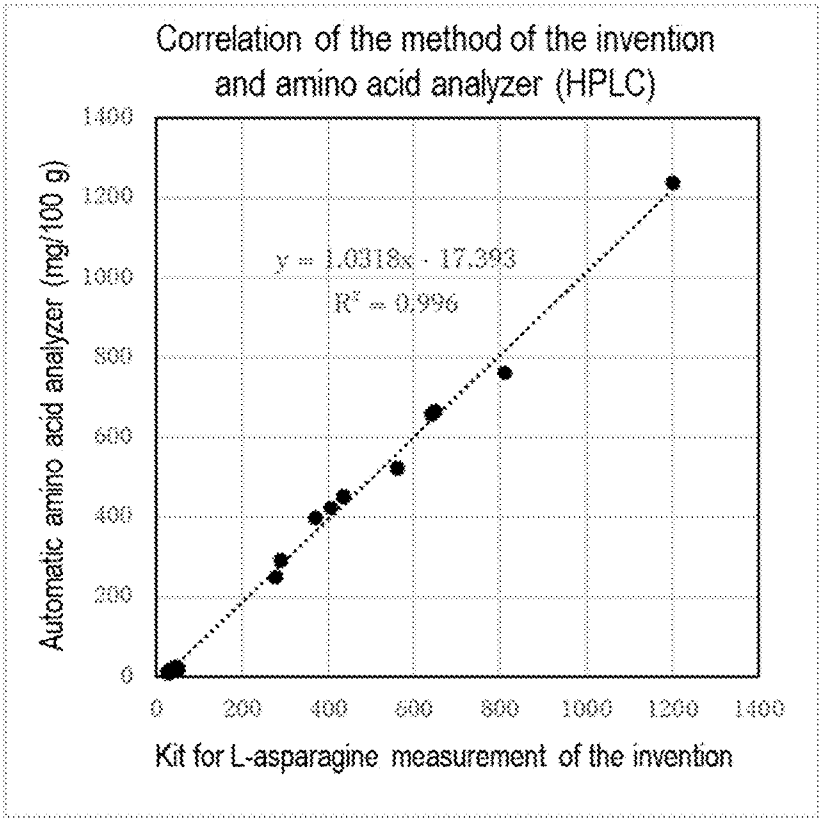

[Fig. 11]
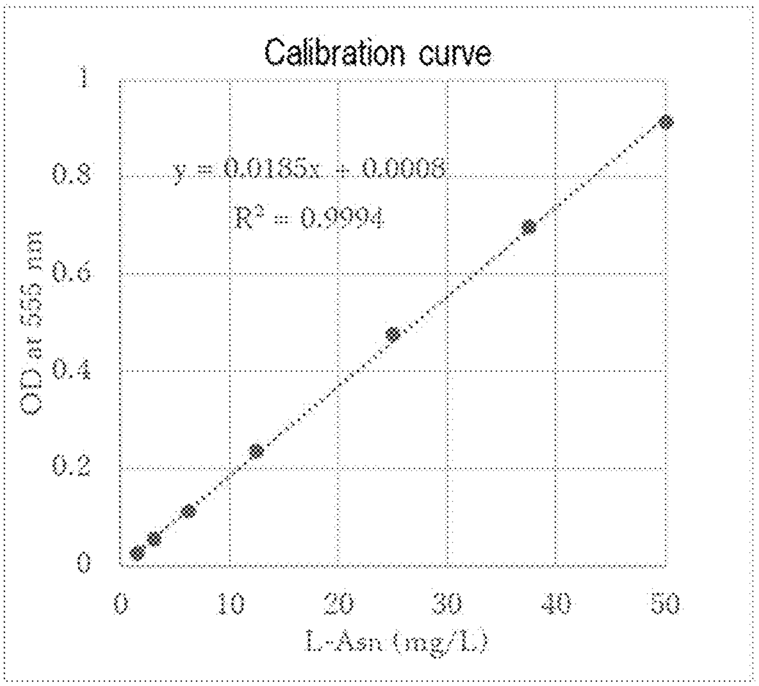

SEQUENCE LISTING

```
Sequence total quantity: 2
SEQ ID NO: 1           moltype = AA  length = 396
FEATURE                Location/Qualifiers
source                 1..396
                       mol_type = protein
                       organism = Escherichia coli
SEQUENCE: 1
MFENITAAPA DPILGLADLF RADERPGKIN LGIGVYKDET GKTPVLTSVK KAEQYLLENE  60
TTKNYLGIDG IPEFGRCTQE LLFGKGSALI NDKRARTAQT PGGTGALRVA ADFLAKNTSV  120
KRVWVSNPSW PNHKSVFNSA GLEVREYAYY DAENHTLDFD ALINSLNEAQ AGDVVLFHGC  180
CHNPTGIDPT LEQWQTLAQL SVEKGWLPLF DFAYQGFARG LEEDAEGLRA FAAMHKELIV  240
ASSYSKNFGL YNERVGACTL VAADSETVDR AFSQMKAAIR ANYSNPPAHG ASVVATILSN  300
DALRAIWEQE LTDMRQRIQR MRQLFVNTLQ EKGANRDFSF IIKQNGMFSF SGLTKEQVLR  360
LREEFGVYAV ASGRVNVAGM TPDNMAPLCE AIVAVL                           396

SEQ ID NO: 2           moltype = DNA  length = 1191
```

-continued

```
FEATURE                 Location/Qualifiers
source                  1..1191
                        mol_type = genomic DNA
                        organism = Escherichia coli
SEQUENCE: 2
atgtttgaga acattaccgc cgctcctgcc gacccgattc tgggcctggc cgatctgttt   60
cgtgccgatg aacgtcccgg caaaattaac ctcgggattg gtgtctataa agatgagacg  120
ggcaaaaccc cggtactgac cagcgtgaaa aaggctgaac agtatctgct cgaaaatgaa  180
accaccaaaa attacctcgg cattgacggc atccctgaat ttggtcgctg cactcaggaa  240
ctgctgtttg gtaaaggtag cgccctgatc aatgacaaac gtgctcgcac ggcacagact  300
ccgggggggca ctggcgcact acgcgtggct gccgatttcc tggcaaaaaa taccagcgtt  360
aagcgtgtgt gggtgagcaa cccaagctgg ccgaaccata agagcgtctt taactctgca  420
ggtctggaag ttcgtgaata cgcttattat gatgcggaaa atcacactct tgacttcgat  480
gcactgatta acagcctgaa tgaagctcag gctggcgacg tagtgctgtt ccatggctgc  540
tgccataacc caaccggtat cgaccctacg ctggaacaat ggcaaacact ggcacaactc  600
tccgttgaga aaggctggtt accgctgttt gacttcgctt accagggttt tgcccgtggt  660
ctggaagaag atgctgaagg actgcgcgct ttcgcggcta tgcataaaga gctgattgtt  720
gccagttcct actctaaaaa ctttggcctg tacaacgagc gtgttggcgc ttgtactctg  780
gttgctgccg acagtgaaac cgttgatcgc gcattcagcc aaatgaaagc ggcgattcgc  840
gctaactact ctaacccacc agcacacggc gcttctgttg ttgccaccat cctgagcaac  900
gatgcgttac gtgcgatttg ggaacaagag ctgactgata tgcgccagcg tattcagcgt  960
atgcgtcagt tgttcgtcaa tacgctgcag gaaaaaggcg caaaccgcga cttcagcttt 1020
atcatcaaac agaacggcat gttctccttc agtggcctga caaaagaaca agtgctgcgt 1080
ctgcgcgaag agtttggcgt atatgcggtt gcttctggtc gcgtaaatgt ggccgggatg 1140
acaccagata acatggctcc gctgtgcgaa gcgattgtgg cagtgctgta a           1191
```

METHOD FOR MEASURING L-ASPARAGINE AND KIT FOR THE SAME

TECHNICAL FIELD

The present invention relates to a method for measuring L-asparagine and a kit for the same.

BACKGROUND ART

L-Asparagine is one of the nonessential amino acids, and, in vivo, it is biosynthesized from L-aspartic acid by asparagine synthetase and degraded into aspartic acid and ammonia by asparaginase. Asparaginase is used as a therapeutic agent for acute leukemia and malignant lymphoma, and studies are being conducted to improve the substrate specificity and stability of asparaginase (Patent documents 1 and 2).

L-Asparagine contained in foods causes an aminocarbonyl reaction (Maillard reaction) with a reducing sugar such as fructose and glucose when heated (120° C. or higher) during cooking, such as frying, baking, and roasting, to generate acrylamide, which has neurotoxicity and carcinogenicity. In the 38th session of Codex Alimentarius Commission held on 2006, the Codex Committee on Food Additives and Contaminants confirmed that acrylamide is contained in many foods, including processed potato products and processed cereal products (Non-patent document 1). In the session of the same commission held on 2009, the "Code of Practice for the Reduction of Acrylamide in Foods (CAC/RCP 67-2009)" was adopted as an international guideline. Since the main causative substance of the acrylamide formation in foods is free L-asparagine, the significance of measuring L-asparagine in foods is going increasing in recent years.

Measurement of L-asparagine is typically performed with an amino acid analyzer utilizing HPLC. Amino acid measurement samples to be charged into amino acid analyzers are often hydrolyzed, and therefore L-asparagine and L-glutamine are often quantified as parts of L-aspartic acid and L-glutamic acid, respectively.

L-asparagine assay kit based on an enzymatic method is already commercially available (Non-patent document 2). However, the detailed scheme of this kit is not specified.

Another L-asparagine assay kit based on an enzymatic method is also commercially available (Non-patent document 3), but this kit is not a kit for measurement of L-asparagine alone, and it is a kit for measuring L-glutamine, L-asparagine, and ammonia in the same reaction system. The principle of the measurement is that ammonia generated from L-glutamine by glutaminase is measured with decreasing absorbance (340 nm) of the coenzyme NADPH used in the L-glutamic acid dehydrogenase reaction to first quantify L-glutamine, and then ammonia generated from L-asparagine by asparaginase is measured in the same manner to quantify L-asparagine.

Furthermore, as an L-asparagine measurement method using enzyme, there has been developed the enzyme sensor method, in which L-asparagine is converted into L-aspartic acid with asparaginase, then the generated L-aspartic acid is oxidized with L-aspartate oxidase, and the generated hydrogen peroxide is measured by the electrode (Patent document 3).

In such circumstances, the inventors of the present invention have developed methods based on a combination of enzymatic cycling reactions using amino acid transaminase and L-glutamate oxidase and peroxidase reaction as methods for measuring 7-aminobutyric acid (GABA), L-aspartic acid and L-alanine, and put them into practical use as measurement kits (Patent document 4 to 6).

PRIOR ART REFERENCES

Patent Documents

Patent document 1: Japanese Patent Publication (Kokai) No. 2010-207168

Patent document 2: Japanese Patent Publication (Kokai) No. 2020-129969

Patent document 3: Japanese Patent Publication (Kokai) No. 2020-202825

Patent document 4: Japanese Patent No. 6585244

Patent document 5: Japanese Patent No. 6703721

Patent document 6: Japanese Patent No. 6703722

Non-Patent Documents

Non-patent document 1: The 38th Session of the Codex Alimentarius Commission, Codex Committee on Food Additives and Contaminants (2006), Discussion Document CX/FAC 06/38/35

Non-patent document 2: Asparagine Assay Kit (Fluorometric), Catalog #K736-100 (BioVision, Inc., 155 S Milpitas Blvd. Milpitas, CA 95035), https://www.biovision.com/documentation/datasheets/K736.pdf Non-patent document 3: L-ASPARAGINE/L-GLUTAMINE/AMMONIA (RAPID) ASSAY PROCEDURE K-ASNAM 04/1, Megazyme Ltd, https://www.megazyme.com/l-asparagine-l-glutamine-ammonia-rapid-assay-ki

SUMMARY OF THE INVENTION

Problems to be Solved by the Invention

The method of the commercial kit mentioned above (Non-patent document 2) is presumably based on such a principle that L-asparagine is converted into L-aspartic acid with asparaginase, the generated L-aspartic acid is converted into pyruvic acid with a certain enzyme, this pyruvic acid is oxidized with pyruvate oxidase, and the generated hydrogen peroxide is measured by a colorimetric or fluorometric method based on the peroxidase reaction. It is presumed that, in this method of which target substances are biological ingredients, L-aspartic acid and pyruvic acid contained in the sample cannot be removed, therefore the backgrounds of L-aspartic acid and pyruvic acid contained in the sample are significant and affects measurement. In such a method the amounts of these substance must be separately measured for subtraction. Also in the case of the enzyme sensor using asparaginase and L-aspartate oxidase, the amount of L-aspartic acid contained in the sample needs to be measured beforehand and subtracted from a measured value.

As an enzymatic method for measuring L-asparagine, a method of treating L-asparagine with asparaginase, converting the generated L-aspartic acid into L-glutamic acid with aspartate transaminase, treating this L-glutamic acid with L-glutamate dehydrogenase or L-glutamate oxidase, and measuring the generated reaction product can be conceived. However, no practical L-asparagine measurement kit using such an enzymatic method has actually been developed. In addition, because foods and biological samples contain relatively large amounts of L-glutamine, the substrate specificity of the asparaginase used first in this method poses a problem. Asparaginase generally shows relatively high reactivity also to L-glutamine and generates L-glutamic acid, and therefore in order to apply this method to the measurement of L-asparagine in a sample, it is necessary to devise a way to distinguish and separate L-asparagine and L-glutamine so that only L-asparagine can be measured. In other words, in the measurement method using asparaginase to convert L-asparagine into L-glutamic acid, it is preferable to remove L-glutamine in advance.

Means for Solving the Problems

The inventors of the present invention invented a novel method for specifically measuring L-asparagine after removing coexisting substances that affect L-asparagine measurement, such as L-glutamic acid, L-aspartic acid, L-glutamine, and ascorbic acid, which are generally contained in foods and biological samples, by utilizing sequential and simultaneous reactions with multiple enzymes, especially the enzymatic cycling method with L-aspartate transaminase and L-glutamate oxidase.

Specifically, the present invention provides the followings.

[1] A kit for measuring L-asparagine contained in a sample, the kit comprising the following solution A and solution B:

(Solution A) a solution containing aspartate transaminase, glutaminase, L-glutamate oxidase, catalase, and α-ketoglutaric acid; and (Solution B) a solution containing asparaginase, peroxidase, and a catalase inactivator;

provided that one of the solution A and solution B contains a coupler compound, and the other contains a new Trinder's reagent.

[2] The kit according to 1, wherein the solution A further contains ascorbate oxidase.

[3] The kit according to 1 or 2, wherein the solution A contains a coupler compound, the solution B contains a new Trinder's reagent, and the solution A further contains pyridoxal phosphate.

[4] The kit according to any one of 1 to 3, wherein the coupler compound is 4-aminoantipyrine.

[5] The kit according to any one of 1 to 4, wherein the new Trinder's reagent is N-ethyl-N-(2-hydroxy-3-sulfopropyl)-3-methylaniline sodium salt (TOOS), or N-ethyl-N-sulfopropylaniline (ALPS).

[6] The kit according to any one of 1 to 5, which further comprises an L-asparagine standard solution.

[7] The kit according to any one of 1 to 6, which comprises a device using an LED light source for measuring amount of a dye generated.

[8] A method for measuring L-asparagine contained in a sample that may contain any selected from the group consisting of L-aspartic acid, L-glutamine, L-glutamic acid, ascorbic acid, and erythorbic acid, the method comprising the following step 1 and step 2:

(Step 1) the step of allowing aspartate transaminase and α-ketoglutaric acid to act on L-aspartic acid to generate L-glutamic acid, allowing glutaminase to act on L-glutamine to generate L-glutamic acid, allowing glutamate oxidase to act on L-glutamic acid to generate α-ketoglutaric acid, allowing catalase to act on generated hydrogen peroxide to decompose it, and allowing ascorbate oxidase to act on ascorbic acid or erythorbic acid to decompose ascorbic acid or erythorbic acid in a container; and (Step 2) the step of allowing a catalase inactivator to act on the catalase to inactivate the catalase, and allowing asparaginase, aspartate transaminase, α-ketoglutaric acid, L-glutamate oxidase, peroxidase, a coupler compound, and a new Trinder's reagent to act on L-asparagine to form a dye, which step is performed following the step 1 in the same container.

[9] The method according to 8, wherein the step 1 and step 2 are performed at 25 to 40° C.

[10] The method according to 8 or 9, wherein the sample is an agricultural product, and the method is for selecting an agricultural product with a low asparagine content as a raw material of a processed food.

Effects of the Invention

In the measurement method or with the measurement kit of the present invention for measuring asparagine, L-glutamine contained in a sample is converted into L-glutamic acid and removed before allowing asparaginase to act on asparagine contained in the sample, and therefore L-asparagine can be specifically measured with eliminating the influence of L-glutamine contained in the sample despite the low specificity of the asparaginase.

In the measurement method or with the measurement kit of the present invention for measuring asparagine, the reactions are continuously performed in the same container. In addition, the method is an end point method and the kit utilizes such a method. Therefore, L-asparagine can be easily and accurately measured.

BRIEF DESCRIPTION OF THE DRAWINGS

FIG. 1A diagram showing the principle of the measurement of L-asparagine (L-Asn) according to the present invention (application of the enzymatic cycling method in both the step 1 using the solution A and the step 2 using the solution B).

FIG. 2 Tune course of the absorbance.

FIG. 3 Relationship between the concentration of L-asparagine and absorbance at 555 nm.

FIG. 4 Color development intensities (%) of amino acids relative to the color development intensity of L-asparagine (100%) observed when the solution A not containing glutaminase was used.

FIG. 5 Color development intensities (%) of amino acids relative to the color development intensity of L-asparagine (100%) observed when the solution A containing glutaminase for decomposing L-glutamine was used.

FIG. 6 Influence of L-aspartic acid.

FIG. 7 Influence of L-glutamic acid.

FIG. 8 Influence of L-glutamine.

FIG. 9 Influence of ascorbic acid.

FIG. 10 Correlation between measured values obtained with the measurement kit mentioned in the example and measured values obtained with an amino acid analyzer (HPLC method).

FIG. 11 Relationship between the concentration of L-asparagine and absorbance at 555 nm observed in the low-concentration measurement method.

MODES FOR CARRYING OUT THE INVENTION (Solutions A and B)

The present invention provides a kit for measuring L-asparagine in a sample, which comprises the following solution A and solution B:

(Solution A) a solution containing aspartate transaminase, glutaminase, L-glutamate oxidase, catalase, and α-ketoglutaric acid; and (Solution B) a solution containing asparaginase, peroxidase, and a catalase inactivator;

provided that one of the solution A and solution B contains a coupler compound, and the other contains a new Trinder's reagent. In one preferred embodiment, the solution A contains the coupler compound and the solution B contains the new Trinder's reagent. The stability of the solutions is thereby improved.

The kit of the present invention can be used to measure L-asparagine in a sample that may contain any selected from the group consisting of L-aspartic acid, L-glutamine, and L-glutamic acid. The solution A may further contain ascorbate oxidase, and such a kit can be used to measure L-asparagine in a sample that may contain ascorbic acid or erythorbic acid.

Specific examples of the aspartate transaminase used in the present invention include aspartate transaminases derived from microorganisms such as *Escherichia coli, Bacillus subtilis, Corynebacterium glutamicum, Mycobacteriun tuberculosis, Pseudomonas aeruginosa, Pseudomonas putida, Thermus thermophilus, Saccharomyces cerevisiae, Saccharolobus solfataricus, Aspergillus oryzae*, and *Strepiomyces griseus*. One of the preferred examples is one expressed by a recombinant *Escherichia coli* using a plasmid constructed by inserting a gene derived from the *Escherichia coli* K12 MG1655 strain (gene number: b0928), and purified with an ion exchange resin column, gel filtration resin column, or the like.

The amino acid sequence (SEQ ID NO: 1) and the gene sequence (SEQ ID NO: 2) of the aspartate transaminase derived from the *Escherichia coli* K-12 MG1655 strain are described below in this order.

[Formula 1]

```
MFENITAAPADPILGLADLFRADERPGKINLGIGVYKDETGKTPVLTSVKKAEQYLLENETTKNYLG
IDGIPEFGRCTQELLFGKGSALINDKRARTAQTPGGTGALRVAADFLAKNTSVKRVWVSNPSWPNHK
SVFNSAGLEVREYAYYDAENHTLDFDALINSLNEAQAGDVVLFHGCCHNPTGIDPTLEQWQTLAQLS
VEKGWLPLFDFAYQGFARGLEEDAEGLRAFAAMHKELIVASSYSKNFGLYNERVGACTLVAADSETV
DRAFSQMKAAIRANYSNPPAHGASVVATILSNDALRAIWEQELTDMRQRIQRMRQLFVNTLQEKGAN
RDFSFIIKQNGMFSFSGLTKEQVLRLREEFGVYAVASGRVNVAGMTPDNMAPLCEAIVAVL.
```

[Formula 2]

```
atgtttgagaacattaccgccgctcctgccgacccgattctgggcctggccgatctgtttcgtgccg
atgaacgtcccggcaaaattaacctcgggattggtgtctataaagatgagacgggcaaaaccccggt
actgaccagcgtgaaaaaggctgaacagtatctgctcgaaaatgaaaccaccaaaaattacctcggc
attgacggcatccctgaatttggtcgctgcactcaggaactgctgtttggtaaaggtagcgccctga
tcaatgacaaacgtgctcgcacggcacagactccgggggcactggcgcactacgcgtggctgccga
tttcctggcaaaaaataccagcgttaagcgtgtgtgggtgagcaacccaagctggccgaaccataag
agcgtctttaactctgcaggtctggaagttcgtgaatacgcttattatgatgcggasaatcacactc
ttgacttcgatgcactgattaacagcctgaatgaagctcaggctggcgacgtagtgctgttccatgg
ctgctgccataacccaaccggtatcgaccctacgctggaacaatggcaaacactggcacaactctcc
gttgagaaaggctggttaccgctgtttgacttcgcttaccagggttttgcccgtggtctggaagaag
atgctgaaggactgcgcgctttcgcggctatgcataaagagctgattgttgccagttcctactctaa
aaactttggcctgtacaacgagcgtgttggcgcttgtactctggttgctgccgacagtgaaaccgtt
gatcgcgcattcagccaaatgaaagcggcgattcgcgctaactactctaacccaccagcacacggcg
cttctgttgttgccaccatcctgagcaacgatgcgttacgtgcgatttgggaacaagagctgactga
tatgcgccagcgtattcagcgtatgcgtcagttgttcgtcaatacgctgcaggaaaaaggcgcaaac
cgcgacttcagctttatcatcaaacagaacggcatqttctccttcagtggcctgacaaaagaacaag
tgctgcgtctgcgcgaagagtttggcgtatatgcggttgcttctggtcgcgtaaatgtggccgggat
gacaccagataacatggctccgctgtgcgaagcgattgtggcagtgctgtaa.
```

(Enzymes)

For the present invention, as the enzymes, known aspartate transaminases, glutaminases, L-glutamate oxidases, catalases, asparaginases, peroxidases, and ascorbate oxidases can be used.

Examples of the asparaginase used in the present invention include asparaginases derived from microorganisms such as *Escherichia coli, Bacillus subtilis, Proteus vulgaris, Pseudomonas aeruginosa, Thermus thermophilus, Saccharomyces cerevisiae, Aspergillus oryzae, Aspergillus niger*, and *Streptomyces fradiae*. One class of the preferred examples is asparaginases derived from bacteria (EC 3.5.1.1). One of the particularly preferred examples is a commercially available asparaginase, the enzyme solution derived from *Aspergillus oryzae* produced by Novozymes (trade name Acrylaway).

Examples of the glutamate oxidase used in the present invention include L-glutamate oxidases derived from microorganisms such as *Streptomyces* sp. X-119-6, *Streptomyces violascens*, and *Streptomyces endus*.

Examples of the glutaminase used in the present invention include glutaminase derived from *Bacillus amyloliquefaciens*, etc.

Examples of the catalase used in the present invention include catalase derived from bovine liver as well as catalases derived from microorganisms such as *Aspergillus niger* and *Corynebacterium glutamicum*.

Examples of the peroxidase used in the present invention include peroxidase derived from horseradish.

Examples of the ascorbate oxidase used in the present invention include ascorbate oxidase derived from cucumber or pumpkin.

(New Trinder's Reagent)

In the present invention, as the new Trinder's reagent, known new Trinder's reagents can be used. Examples of the new Trinder's reagent used in the present invention include N-ethyl-N-(2-hydroxy-3-sulfopropyl)-3-methylaniline sodium salt (TOOS), N-ethyl-N-(2-hydroxy-3-sulfopropyl)-3-methoxyaniline (ADOS), N-(2-hydroxy-3-sulfopropyl)-3,5-dimethoxyaniline (HDAOS). N-ethyl-N-sulfopropyl-3-methoxyaniline (ADPS), N-ethyl-N-sulfopropylaniline (ALPS), N-ethyl-N-sulfopropyl-3-methylaniline (TOPS), N-ethyl-N-(2-hydroxy-3-sulfopropyl)-3,5-dimethylaniline (MAOS), N-ethyl-N-sulfopropyl-3,5-dimethoxyaniline (DAPS). N-(2-carboxyethyl)-N-ethyl-3,5-dimethoxyaniline (CEDB), N-(2-carboxyethyl)-N-ethyl-3-methoxyaniline (CEMO), N-ethyl-N-(2-hydroxy-3-sulfopropyl)-3,5-dimethoxy-4 fluoroaniline (FDAOS), and N-ethyl-N-sulfopropyl-3,5-dimethoxy-4-fluoroaniline (FDAPS). It is preferable to use any of N-ethyl-N-(2-hydroxy-3-sulfopropyl)-3-methylaniline sodium salt (TOOS), N-ethyl-N-(2-hydroxy-3-sulfopropyl)-3-methoxyaniline (ADOS), N-(2-hydroxy-3-sulfopropyl)-3,5-dimethoxyaniline (RDAOS), N-ethyl-N-sulfopropyl-3-methoxyaniline (ADPS), N-ethyl-N-sulfopropylaniline (ALPS), N-ethyl-N-sulfopropyl-3-methylaniline (TOPS), and N-ethyl-N-(2-hydroxy-3-sulfopropyl)-3,5-dimethylaniline (MAOS), and it is more preferable to use N-ethyl-N-(2-hydroxy-3-sulfopropyl)-3-methylaniline sodium salt (TOOS).

(Coupler Compound)

In the present invention, as the coupler compound, known coupler compounds can be used. In the present invention, any compound that causes color development in combination with the new Trinder's reagent may be used, and examples include 4-aminoantipyrine (4-AA), vanillindiaminesulfonic acid, methylbenzothiazolinone hydrazone (MBTH), sulfonated methylbenzothiazolinone hydrazone (SMBTH), aminodiphenylamine-1-(4-sulfophenyl)-2,3-dimethyl-4-amino-5-pyrazolone (CP2-4), N-ethyl-N-(2-hydroxy-3-sulfopropyl)-m-toluidine and derivatives thereof. It is preferable to use 4-aminoantipyrine (4-AA).

(Other Ingredients)

The solution A included in the kit of the present invention may further contain pyridoxal phosphate, a coenzyme of transaminase, to stabilize the enzymes. The solution B may further contain a preservative. As the preservative, known preservatives may be used. Examples include sodium azide, ProClin 300, ProClin 950, and chloramphenicol.

The solution A and solution B may contain an ingredient having a pH-buffering ability. Examples of such an ingredient include acetates, phosphates, citrates, borates, tartrates, Tris(tris(hydroxymethyl)aminoethane), and Hepes ([2-[4-(2-hydroxyethyl)-1-piperazinyl]ethanesulfonic acid]).

(Contents of Ingredients)

The contents of the enzymes, coupler compound, etc. contained in the solution A are preferably in the following ranges: 0.1 to 10 U/mL of aspartate transaminase, 0.05 to 3 U/mL of glutaminase, 0.1 to 2 U/mL of glutamate oxidase, 500 to 2,000 U/mL of catalase, and 0.1 to 2.0 μmol/mL of the coupler compound, and especially, they are more preferably in the following ranges: 0.5 to 2 U/mL of aspartate transaminase, 0.2 to 1 U/mL of glutaminase, 0.4 to 1 U/mL of glutamate oxidase, 1,000 to 1,500 U/mL of catalase, and 0.2 to 1.0 μmol/mL of the coupler compound. The content of α-ketoglutaric acid can be 1 to 6 μmol/mL, preferably 2 to 3 μmol/ml. The content of pyridoxal phosphate can be 0.005 to 0.05 μmol/mL, preferably 0.01 to 0.02 μmol/mL. The content of ascorbate oxidase can be 5 to 30 U/mL, preferably 10 to 20 U/mL.

The contents of the enzymes, new Trinder's reagent, and catalase inactivator contained in the solution B are preferably in the following ranges: 2 to 20-fold dilution for asparaginase, 5 to 20 U/mL of peroxidase, 0.1 to 2.0 μmol/mL of the new Trinder's reagent, and 0.01 to 0.09% of the catalase inactivator, especially preferably, 5 to 10-fold dilution for asparaginase, 10 to 15 U/mL of peroxidase, 0.2 to 1.0 μmol/mL of the new Trinder's reagent, and 0.05 to 0.09% of the catalase inactivator.

(L-Asparagine Standard Solution)

In addition to the solutions A and B mentioned above, the kit of the present invention may also contain an L-asparagine standard solution. The concentration of the L-asparagine standard solution can be determined as appropriate, but it is preferably a concentration around the upper limit of the measurement of the kit from the viewpoint that serial dilution is performed for the preparation of a calibration curve for the measurement. Specifically, it can be, for example, 100 to 200 mg/mL, preferably 100 mg/mL.

(Other Components of the Kit)

The kit of the present invention may also comprise a dropper for collection of the solution A, a dropper for collection of the solution B, a colorimeter with LED as a light source for measuring the amount of dye generated, and a plastic cuvette for the measurement.

Use

The sample as the object of the measurement according to the present invention is not particularly limited as long as it is expected to contain L-asparagine. Specific examples include agricultural products, livestock products, marine products, alcoholic beverages such as sake and beer, food raw materials, processed foods, culture of cells, microorganisms etc., and biological samples such as blood, body fluids and tissue extracts. Examples of agricultural products include fruits (e.g., those of cherry, peach, plum, grape, fig, apple, orange, melon, pineapple, banana, kiwi, strawberry, avocado, etc.), vegetables (tomato, asparagus, bean sprouts, pumpkin, renkon (lotus root), cabbage, spinach, carrot, radish, etc.), legumes (soybean, pea, etc.), potatoes (potato, sweet potato, etc.), grains (wheat, oat, rye, barley, rice, buckwheat, corn, etc.), seeds (peanuts, almonds, cashew nuts, etc.), coffee beans, cacao beans, tea leaves, etc. Examples of the food raw materials include wheat flour.

Steps

The reactions for measuring L-asparagine in a sample using the kit of the present invention comprises the following steps 1 and 2:

(Step 1) the step of allowing aspartate transaminase and α-ketoglutaric acid to act on L-aspartic acid to generate L-glutamic acid, allowing glutaminase to act on L-glutamine to generate L-glutamic acid, allowing glutamate oxidase to act on L-glutamic acid to generate α-ketoglutaric acid, allowing catalase to act on generated hydrogen peroxide to decompose it, and allowing ascorbate oxidase to act on ascorbic acid or erythorbic acid to decompose ascorbic acid or erythorbic acid in a container; and (Step 2) the step of allowing a catalase inactivator to act on the catalase to inactivate the catalase, and allowing asparaginase, aspartate transaminase, α-ketoglutaric acid, L-glutamate oxidase, peroxidase, coupler compound, and new Trinder's reagent to act on L-asparagine to form a dye, which step is performed following the step 1 in the same container.

In the present invention, in order to measure the target amino acid, the step 1 is performed first by adding the solution A to a sample in a container. As a result, L-aspartic acid contained in the sample is removed by the enzymatic cycling method using aspartate transaminase, L-glutamate oxidase, and catalase, and L-glutamine contained in the sample is converted into L-glutamic acid by glutaminase at the same time. Further, L-glutamic acid originally coexisting in the sample and L-glutamic acid generated by aspartate transaminase or glutaminase are decomposed by the simultaneously proceeding reactions with L-glutamate oxidase and catalase, and ascorbic acid or erythorbic acid contained in the sample is decomposed by ascorbate oxidase.

In the step 1, if the sample does not contain L-aspartic acid, the aspartate transaminase is not allowed to act on L-aspartic acid to generate L-glutamic acid, if the sample does not contain L-glutamine, the L-glutaminase is not allowed to act on L-glutamine to generate L-glutamic acid, and if the sample does not contain ascorbic acid or erythorbic acid, the ascorbate oxidase is not allowed to act on ascorbic acid or erythorbic acid to decompose ascorbic acid or erythorbic acid.

In the present invention, after the reactions with the solution A have proceeded sufficiently, the step 2 is carried out by adding the solution B. In the step 2, only L-asparagine, the target of the measurement in the sample, is converted into L-aspartic acid with the asparaginase contained in the solution B, and the resulting L-aspartic acid is converted into L-glutamic acid with the aspartate transaminase from the solution A. The resulting L-glutamic acid is further decomposed with the L-glutamate oxidase from the solution A to generate hydrogen peroxide, which is reacted with a color-developing agent and peroxidase to develop color. In this step 2, the catalase from the solution A is inactivated by the catalase inactivator contained in the solution B, and therefore the color development reaction is not inhibited by the catalase.

The reaction conditions for the steps 1 and 2 can be appropriately set on the basis of the optimum pHs of the respective enzymes used and the temperatures at which the enzymatic reactions proceeds efficiently. Both the steps can be performed at a temperature of 25° C. to 40° C. and pH of 6.5 to 9.0 for 10 to 30 minutes. In a preferred embodiment, at least one of the steps 1 and 2, preferably the both steps, are performed at 25 to 40° C.

The color development caused in the step 2 can be measured as absorbance at a specific wavelength by a general method, for example, by using a spectrophotometer using a light source such as a halogen lamp or xenon lamp. The degree of the color development can also be measured as an electrical signal (e.g., voltage value) with a colorimeter using an LED of a wavelength in a specific range as the light source and a phototransistor or the like as the light-receiving unit. When an LED is used as the light source, the wavelength of the light source used to measure the color development can be selected according to the type of the color-developing agent used. For example, when TOOS is used as the new Trinder's reagent, the absorption maximum of the dye to be generated is 555 nm, and therefore a pure green light LED at 555 nm is suitable as the light source. The concentration of L-asparagine in the sample can be calculated on the basis of the measured value by comparing it with values for known concentrations of L-asparagine measured beforehand.

(Characteristics)

According to the present invention, in the step 1 using the solution A, the enzymatic cycling reactions with aspartate transaminase and L-glutamate oxidase are coupled with the catalase reaction. In the following step 2 performed in the same container with the solution B, the enzymatic cycling reactions with aspartate transaminase and L-glutamate oxidase that were performed in the step 1 are performed again in the presence of the catalase inactivator, and they are coupled with the dye formation reaction with peroxidase and the color-developing agent. There is no other amino acid measurement method that utilizes sequential reactions catalyzed by multiple enzymes, but occur substantially simultaneously, like the method of the present invention utilizing a combination of multiple enzymes in the steps 1 and 2.

One of the characteristics of the present invention is that the enzymatic cycling method using aspartate transaminase and L-glutamate oxidase is performed in the first step for removing L-aspartic acid in the target sample. In the conventional GABA. L-aspartic acid, and L-alanine measurements (Patent documents 4 to 6), the enzymatic cycling method is performed in the second step. However, according to the present invention, by performing the enzymatic cycling method in the step 1 using the solution A, all of L-glutamic acid in the container including not only L-glutamic acid generated from L-aspartic acid contained in the sample, but also L-glutamic acid originally contained in the sample and L-glutamic acid generated from L-glutamine can be decomposed and removed.

Another characteristic of the present invention is that the enzymatic cycling method using aspartate transaminase and L-glutamate oxidase is performed in both of the step 1 (in the presence of catalase) and the step 2 (in the presence of the catalase inhibitor). The same enzymatic cycling method is used for the removal of L-aspartic acid in the step 1 and for the production of hydrogen peroxide of the same moles as that of L-aspartic acid as the target of the measurement in step 2.

Another characteristic of the present invention is that glutaminase is contained in the solution A to solve the problem of the low substrate specificity of asparaginase (see FIGS. 4 and 5). Without glutaminase, asparaginase also acts on L-glutamine coexisting in the sample during the reactions that proceed at room temperature after the addition of the solution B containing asparaginase. According to the present invention, prior to the measurement of L-asparagine in the sample, L-glutamine in the sample is converted into L-glutamic acid by adding the solution A to the sample and removed.

One of the other characteristics of the present invention is that only L-asparagine can be specifically measured, even if L-aspartic acid, L-glutamine, and L-glutamic acid are contained in the sample. L-Aspartic acid, L-glutamine, and L-glutamic acid, and L-asparagine as the target of the measurement are amino acids that constitute proteins and coexist in foods and biological samples, although there are differences in degrees. In particular, L-glutamine is the amino acid most universally present in large amounts in vegetables, blood, etc., and is an amino acid similar to L-asparagine as a carrier of $NH_3$.

Another characteristic of the present invention is that L-asparagine is measured by a so-called endpoint method by coupling the enzyme cycling method with the catalase reaction or oxidase reaction (see FIG. 2). That is, it is thought that, even when using transaminase that does not have a very low Km value for L-aspartic acid generated from L-asparagine, in the reaction of generating L-glutamine by consuming L-aspartic acid and α-ketoglutaric acid, the generated L-glutamic acid is rapidly oxidized and decomposed by L-glutamate oxidase having a low Km value and high activity, and thus the reaction catalyzed by the transaminase proceeds to the direction of more efficiently generating L-glutamic acid.

Further, the reaction catalyzed by L-glutamate oxidase also generates α-ketoglutaric acid, which is again used in the reaction catalyzed by transaminase (see FIG. 1). Therefore, in the end, all of the target amino acid in the sample is used for the reactions, and accurate measurement results can be obtained. It is known that, in endpoint assays using an enzyme, the time until the endpoint is reached becomes shorter as the Km value of the enzyme used becomes smaller and the Vmax becomes larger. In general, the Km value of transaminase is not a Km value suitable for the endpoint method. Further, the reaction catalyzed by transaminase is generally reversible (see Enzyme Handbook, 3rd Edition, Asakura Shoten (2008), p.414, EC 2.6.1.19). Therefore, it is usually difficult to perform endpoint measurements of target amino acids using transaminase.

(Problems of Conventional Methods, Etc.)

As described above, the method of Non-patent document 2 utilized in the commercial kit is presumably based on such a principle that L-asparagine is converted into L-aspartic acid with asparaginase, the generated L-aspartic acid is converted into pyruvic acid with a certain enzyme, this pyruvic acid is oxidized with pyruvate oxidase, and the generated hydrogen peroxide is measured by a colorimetric or fluorometric method based on the peroxidase reaction. It is considered that, in this method of which target substances are biological ingredients, L-aspartic acid and pyruvic acid contained in the sample cannot be removed, therefore the backgrounds of L-aspartic acid and pyruvic acid contained in the sample are significant, and these substances must be separately measured for subtraction. Also in the case of the enzyme sensor using asparaginase and L-aspartate oxidase, the amount of L-aspartic acid contained in the sample also needs to be measured beforehand and subtracted.

As another enzymatic method for measuring L-asparagine, there is a method of treating L-asparagine with asparaginase and measuring generated ammonia. In the aforementioned method of Non-patent document 3 used in the commercial kit, the generated ammonia is measured by using L-glutamate dehydrogenase, but because asparaginase also shows a relatively high cross-reactivity to L-glutamine, it relies on such a complicated operation procedure that a large excess amount of glutaminase is first allowed to act on L-glutamine contained in the sample to decompose L-glutamine, then L-asparagine is decomposed with the action of asparaginase, and ammonia generated in each step is measured in terms of decrease in absorbance of NADP caused by the reaction catalyzed by IL-glutamate dehydrogenase. In addition, since the reaction system of this measurement kit does not generate color, it cannot enable rough visual measurement.

As another theoretical method of using asparaginase for the measurement of L-asparagine, a method of converting generated L-aspartic acid into L-glutamic acid with aspartate transaminase, treating this L-glutamic acid with L-glutamate dehydrogenase or L-glutamate oxidase, and measuring a generated reaction product can be conceived. However, also in this case, L-aspartic acid and L-glutamic acid coexisting in the sample must be removed beforehand. Therefore, no practical L-asparagine measurement kit using such an enzymatic method has actually been developed.

Food samples such as agricultural products and biological samples contain relatively large amounts of L-glutamic acid, L-aspartic acid and L-glutamine along with L-asparagine. Therefore, when asparaginase and aspartate transaminase are used for the measurement of L-asparagine, since asparaginase also shows relatively high reactivity to L-glutamine, it is necessary to devise a way to remove not only L-aspartic acid and L-glutamic acid, but also L-glutamine contained in the sample beforehand, so that only L-asparagine can be measured.

In the method of the present invention, after removing relevant amino acids that coexist in food samples or biological samples and affect the measurement, asparaginase is allowed to act on L-asparagine, the generated L-aspartic acid is converted into L-glutamic acid with L-aspartate transaminase, and finally only L-asparagine can be measured by measuring L-glutamic acid. A practical method for measuring L-asparagine based on such an enzymatic method and a kit for the same are first provided by the present invention.

EXAMPLES

(Example 1) Configuration of Kit

Exemplary compositions of the solution A and the solution B of the L-asparagine measurement kit are shown in Table 1. As asparaginase, an enzyme solution derived from *Aspergillus oryzae* manufactured by Novozymes (trade name Acrylaway) was used.

TABLE 1

Compositions of solution A and solution B

| Solution A | Concentration |
|---|---|
| L-Aspartate transaminase | 1.0 U/ml |
| Catalase | 1,200 U/ml |
| Ascorbate oxidase | 10 U/ml |
| L-Glutamate oxidase | 0.8 U/ml |
| Glutaminase | 0.3 U/ml |
| PLP (pyridoxal phosphate monohydrate) | 0.01 mM |
| α-KG (α-ketoglutaric acid) | 2 mM |
| 4-AA (4-aminoantipyrine) | 0.8 mM |
| ProCiln 950 | 2,000-Fold dilution |

TABLE 1-continued

| Compositions of solution A and solution B | |
|---|---|
| 1M Tris, pH 8.4 | 50 mM |
| Sterile filtered distilled water | |
| **Solution B** | **Concentration** |
| Asparaginase | 10-Fold dilution |
| Peroxidase | 10 U/ml |
| $NaN_3$ | Lower than 0.9 mg/ml |
| TOOS | 0.8 mM |
| 1M HEPES, pH 7.5 | 200 mM |
| Sterile filtered distilled water | |

(Example 2) Time Course of Color Development

With the measurement kit of the present invention, a dye is finally generated from L-asparagine by various enzymatic reactions. The time course of the color development at room temperature was examined to confirm that the conversion reactions from L-asparagine and dye formation completely reached the endpoint by sequentially and simultaneously performing the reactions in the same container.

The measurement was performed according to the following procedure by using a solution having an L-asparagine concentration of 100 mg/L as a test sample. First, 0.05 mL of the L-asparagine solution was placed in a 1 cm-square disposable cuvette, 0.5 mL of the solution A was added, the mixture was left at room temperature for 10 minutes, then 0.5 mL of the solution B was added, and the change in absorbance at 555 nm at room temperature was measured with an absorbance-displaying type LED colorimeter.

FIG. 2 shows the time course of the absorbance. The absorbance became constant about 9 minutes after the start of the reaction and was constant thereafter. Therefore, it was demonstrated that the measurement of L-asparagine according to the present invention is performed as a so-called endpoint method.

(Example 3) Calibration Curve

A calibration curve was prepared by using solutions having L-asparagine concentrations ranging from 12.5 to 200 mg/L as test samples. The measurement was performed according to the following procedure. First, 0.05 mL of L-asparagine solution of each concentration was placed in a 1 cm-square disposable cuvette, 0.5 mL of the solution A was added, the reactions were allowed for 10 minutes at room temperature, then 0.5 mL of the solution B was added, and the reactions were allowed at room temperature for further 10 minutes. After completion of the reactions, absorbance was measured at 555 nm with an absorbance-displaying type LED colorimeter. The absorbance of water as a blank was also measured. A calibration curve was prepared with the values obtained after subtraction of the value for the blank.

The relationship between the concentration of L-asparagine and the absorbance at 555 nm was represented as a straight line with a correlation coefficient of 0.9996, as shown in FIG. 3.

(Example 4) Evaluation of Substrate Specificity

Existing asparaginases have been found to show relatively high reactivity to L-glutamine as well. It was confirmed whether only L-asparagine can be specifically measured by adding glutaminase for decomposing L-glutamine to the solution A to remove the reactions with L-glutamine.

The measurement was performed according to the following procedure. First, each of 20 types of amino acid solutions (1 mM) was placed in a 1 cm-square disposable cuvette in a volume of 0.05 mL, 0.5 mL of either the solution A not containing glutaminase or the solution A containing 0.5 U/mL of glutaminase was added, the reactions were allowed at room temperature for 10 minutes, then 0.5 ml of the solution B was added, and the reactions were allowed at room temperature for further 10 minutes. After completion of the reactions, the absorbance was measured at 555 nm with an absorbance-displaying type LED colorimeter, and degree of the color development for each amino acid relative to the degree of the color development for L-asparagine (100%) was calculated with the value obtained after subtraction of the absorbance of water as a blank.

When the solution A not containing glutaminase was used, about 18% of color development was observed for L-glutamine, but the addition of glutaminase for decomposing L-glutamine to the solution A almost completely eliminated the side reactions. The degrees of color development for other amino acids were 2% or less relative to that for L-asparagine, and thus the measurement method specific for L-asparagine was established (FIGS. 4 and 5).

The experiment method is shown below.

TABLE 2

| |
|---|
| 1 mM Solution of each substrate (50 μL) |
| ↓ ← Solution A (0.5 mL) |
| Leaving for 10 minutes |
| ↓ ← Solution B (0.5 mL) |
| Leaving for 10 minutes |
| ↓ |
| Measurement of absorbance (λ = 555 nm) |

This result confirmed the effectiveness of the addition of glutaminase. Therefore, the present invention is applicable to the measurement of L-asparagine in samples that are assumed to contain L-glutamine, such as food products.

(Example 5) Evaluation of Influences of Amounts of Coexisting L-Glutamine, L-Glutamic Acid, L-Aspartic Acid, and Ascorbic Acid The experiment method is shown below.

TABLE 3

| |
|---|
| L-Asn solution (100 mg/L) containing 0 to 200 mg/L of additive (0.05 mL) |
| ↓ ← Solution A (0.5 mL) |
| Leaving for 10 minutes |
| ↓ ← Solution B (0.5 mL) |
| Leaving for 10 minutes |
| ↓ |
| Measurement of absorbance (λ = 555 nm) |

As shown in FIGS. 6 to 9, it was found that measurement values of the absorbance for L-asparagine are not affected by the presence of L-glutamine, L-glutamic acid, L-aspartic acid, and ascorbic acid in the samples at various concentrations.

(Example 6) Measurement of Free L-Asparagine in Agricultural Products

Water was added to samples of tomato, melon and so forth in a 10-fold volume, and the mixtures were subjected to mixing with a mixer for 1 minute. Each juice was centrifuged, and free L-asparagine concentration of the resulting supernatant as a water extraction sample was measured according to the method shown in Table 4 by using the calibration curve shown in Example 3. Measurement of free L-asparagine in the same samples by an amino acid analyzer (HPLC) was also entrusted to Japan Food Research Laboratories.

TABLE 4

| |
|---|
| Standard solution or water extract of agricultural product (0.05 mL) |
| ↓ ← Solution A (0.5 mL) |
| Leaving for 10 minutes |
| ↓ ← Solution B (0.5 mL) |
| Leaving for 10 minutes |
| ↓ |
| Measurement of absorbance (λ = 555 nm) |

As shown in Table 5 and FIG. 10, the L-asparagine measurement values obtained with the measurement kit of this example showed high correlation with L-asparagine measurement values obtained by the external analytical laboratory using an amino acid analyzer (HPLC).

TABLE 5

| | | L-Asparagine (mg/100 g) | |
|---|---|---|---|
| Sample No. | Product | Measurement kit of the invention | Automatic amino acid analyzer |
| 1 | Melon 1 | 30 | 13 |
| 2 | Melon 2 | 30 | 9 |
| 3 | Cherry 1 | 1200 | 1237 |
| 4 | Cherry 2 | 276 | 250 |
| 5 | Tomato 1 | 26 | 11 |
| 6 | Tomato 2 | 28 | 13 |
| 7 | Tomato 3 | 34 | 17 |
| 8 | Asparagus 1 | 288 | 292 |
| 9 | Asparagus 1 | 436 | 453 |
| 10 | Bean sprouts | 404 | 423 |
| 11 | Pumpkin 1 | 50 | 19 |
| 12 | Pumpkin 2 | 46 | 25 |
| 13 | Lotus root 1 | 640 | 658 |
| 14 | Lotus root 2 | 650 | 667 |
| 15 | Lotus root 3 | 810 | 763 |
| 16 | Lotus root 4 | 370 | 397 |
| 17 | Lotus root 5 | 560 | 522 |

(Example 7) Measurement of Free L-Asparagine in Flour

Water was added to flour in a 10-fold volume, and the mixture was subjected to stirring with a stirrer for 1 hour. This suspension was centrifuged, and free L-asparagine concentration of the resulting supernatant used as a water extraction sample of flour was measured according to the measurement method for measuring L-asparagine at a low concentration shown in Table 6 by using the calibration curve shown in FIG. 11 for low concentration measurement. Measurement of free L-asparagine in the same samples by an amino acid analyzer (HPLC) was also entrusted to Japan Food Research Laboratories.

TABLE 6

| |
|---|
| Standard solution or water extract of agricultural product (0.05 mL) |
| ↓ ← Solution A (0.5 mL) |
| Leaving for 10 minutes |
| ↓ ← Solution B (0.5 mL) |
| Leaving for 10 minutes |
| ↓ |
| Measurement of absorbance (λ = 555 nm) |

As shown in Table 7, the L-asparagine measurement values obtained with the measurement kit of the present invention were substantially equivalent to the L-asparagine measurement values obtained by the analytical laboratory using an amino acid analyzer (HPLC) with a correlation coefficient of 0.934.

TABLE 7

| Wheat flour Sample No. | Measurement kit of the invention (mg/100 g) | Automatic amino acid analyzer (HPLC) (mg/100 g) |
|---|---|---|
| 1 | 9.0 | 7.7 |
| 2 | 10.8 | 10.4 |
| 4 | 5.5 | 4.9 |
| 5 | 7.0 | 5.5 |
| 6 | 5.0 | 4.4 |
| 7 | 12.3 | 9.7 |
| 9 | 12.8 | 14.5 |

Sequences Mentioned in Sequence Listing

SEQ ID NO: 1, amino acid sequence of the aspartate transaminase derived from *Escherichia coli* K-12 MG1655

SEQ ID NO: 2, nucleotide sequence of the gene encoding the aspartate transaminase derived from *Escherichia coli* strain K-12 MG1655

The invention claimed is:

1. A kit for measuring L-asparagine contained in a sample, the kit comprising the following solution A and solution B:

(Solution A) a solution containing aspartate transaminase, glutaminase, L-glutamate oxidase, catalase, and α-ketoglutaric acid; and (Solution B) a solution containing asparaginase, peroxidase, and a catalase inactivator;

provided that one of the solution A and solution B contains a coupler compound, and the other contains a new Trinder's reagent.

2. The kit according to claim 1, wherein the solution A further contains ascorbate oxidase.

3. The kit according to claim 1, wherein the solution A contains a coupler compound, the solution B contains a new Trinder's reagent, and the solution A further contains pyridoxal phosphate.

4. The kit according to claim 1, wherein the coupler compound is 4-aminoantipyrine.

5. The kit according to claim 1, wherein the new Trinder's reagent is N-ethyl-N-(2-hydroxy-3-sulfopropyl)-3-methylaniline sodium salt (TOOS), or N-ethyl-N-sulfopropylaniline (ALPS).

6. The kit according to claim 1, which further comprises an L-asparagine standard solution.

7. The kit according to claim 1, which comprises a device using an LED light source for measuring amount of a dye generated.

8. A method for measuring L-asparagine contained in a sample that may contain any selected from the group consisting of L-aspartic acid, L-glutamine, L-glutamic acid, ascorbic acid, and erythorbic acid, the method comprising the following step 1 and step 2:

(Step 1) the step of allowing aspartate transaminase and α-ketoglutaric acid to act on L-aspartic acid to generate L-glutamic acid, allowing glutaminase to act on L-glutamine to generate L-glutamic acid, allowing glutamate oxidase to act on L-glutamic acid to generate α-ketoglutaric acid, allowing catalase to act on generated hydrogen peroxide to decompose it, and allowing ascorbate oxidase to act on ascorbic acid or erythorbic acid to decompose ascorbic acid or erythorbic acid in a container; and (Step 2) the step of allowing a catalase inactivator to act on the catalase to inactivate the catalase, and allowing asparaginase, aspartate transaminase, α-ketoglutaric acid, L-glutamate oxidase, peroxidase, a coupler compound, and a new Trinder's reagent to act on L-asparagine to form a dye, which step is performed following the step 1 in the same container.

9. The method according to claim 8, wherein the step 1 and step 2 are performed at 25 to 40° C.

10. The method according to claim 8, wherein the sample is an agricultural product, and the method is for selecting an agricultural product with a low asparagine content as a raw material of a processed food.

* * * * *